United States Patent [19]

Liebman

[11] Patent Number: 4,741,434
[45] Date of Patent: May 3, 1988

[54] KEY HOLDER WITH ATTACHED CONDOM CASE

[76] Inventor: Herman Liebman, 4704 Satinwood Trail, Coconut Creek, Fla. 33063

[21] Appl. No.: 61,723

[22] Filed: Jun. 15, 1987

[51] Int. Cl.[4] ...................... B65D 85/08; B65D 85/14; A45C 11/00
[52] U.S. Cl. ...................................... 206/38; 206/38.1; 206/69; 220/4 E
[58] Field of Search ......................... 206/37, 37.1–37.8, 206/69, 38, 38.1; 220/4 E

[56] References Cited

U.S. PATENT DOCUMENTS

| | | | |
|---|---|---|---|
| 2,710,114 | 6/1955 | Waber et al. | 206/37 R |
| 3,111,152 | 11/1963 | Goessling | 206/38.1 |
| 3,263,804 | 8/1966 | Marenchin | 206/38 X |
| 3,657,909 | 4/1972 | Boswell | 206/38.1 X |
| 3,918,503 | 11/1975 | Bundy | 206/38.1 |
| 4,166,489 | 9/1979 | Lemelson | 206/38.1 |
| 4,425,997 | 1/1984 | Grant | 220/4 E X |

FOREIGN PATENT DOCUMENTS 1480344 4/1967 France .................................. 206/38

Primary Examiner—William Price
Attorney, Agent, or Firm—John S. Schneider

[57] ABSTRACT

A case for carrying a condom is attached to a key holder. The case is made of two identically configured matable members each having an engageable, peripheral shoulder surrounding a recessed inner surface to form an enclosed space when engaged. Each member is provided with means having openings through which continuous holder means extend. Means are formed on said members for releasably locking them together. Each member may be made of transparent or of opaque material.

1 Claim, 1 Drawing Sheet

KEY HOLDER WITH ATTACHED CONDOM CASE

The present invention generally concerns key chains, key rings and the like. More particulary, this invention relates to a plastic case or receptacle for containing and carrying a condom or condoms attached to a key chain or ring.

A primary object of this invention is to provide a readily accessible condom carrying case. The case is conveniently attached to a key ring or chain to which car, house or other often used keys may be attached.

DESCRIPTION OF THE PREFERRED EMBODIMENTS

Figure 1:
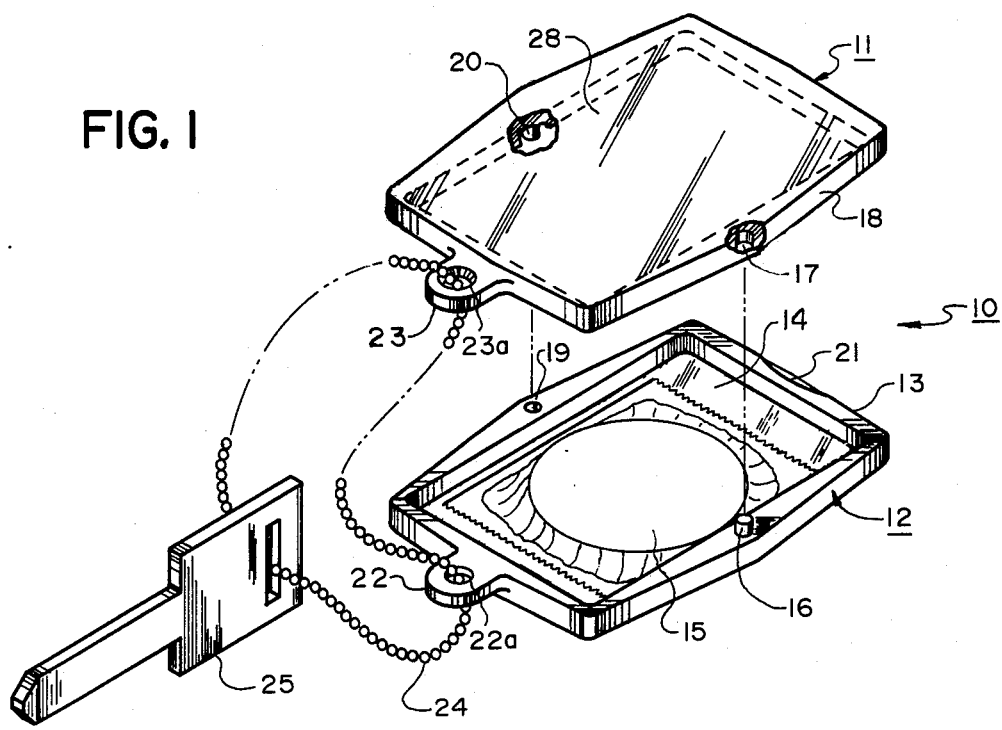
FIG. 1 is an exploded perspective view of the condom carrying case of the invention attached to a key chain.

Referring to FIG. 1 there is shown a case or receptacle, generally designated 10, formed of two identically configured body members 11 and 12. Each of these bodymembers (member 12 is also shown in FIGS. 3 through 6) is preferably rectangularly shaped and formed by any suitable commercially available plastic material. Peripheral shoulders 13 and 18 surround the recessed flat surfaces 14 (inner) and 28 (outer) respectively. A condom package 15 is shown positioned on inner surface 14. Portions of shoulders 13 and 18 along the two opposing longer sides of members 11 and 12 are enlarged or widened and contain engageable locking pins and apertures or holes 16–17 and 19–20. A curved recess 21 shown in shoulder 13 on one end of members 12 matches a similar recess (numeral 9 in FIG. (2) in shoulder 18 on one end of member 11. These recesses facilitate "fingernail" separation of the members and, thereby, opening of the case. The other ends of the members form ears 22 and 23 having openings 22a and 23a, respectively, therethrough. A continuous or endless key chain 24 containing a key 25 is strung through those openings, as shown.

Figure 2:
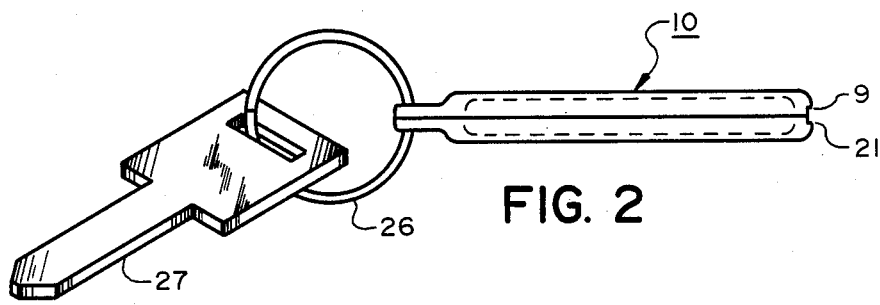
FIG. 2 is side view of the case in closed position attached to a key ring.
Figure 3:
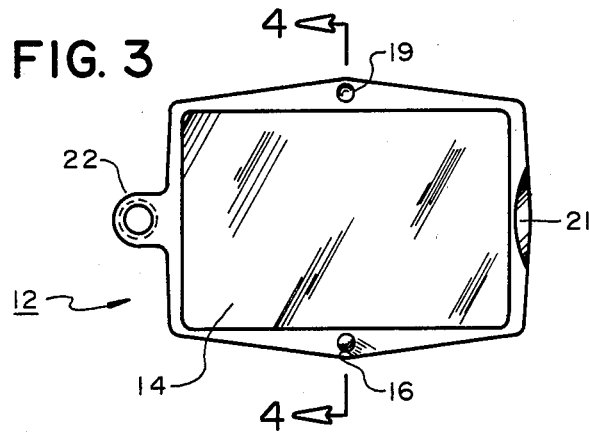
FIG. 3 is a top view of the inner side of one of the two identical body members of the case.
Figure 4:
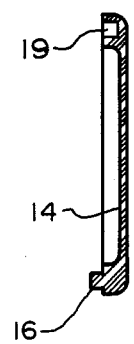
FIG. 4 is a view taken on lines 4—4 of FIG. 3.
Figure 5:
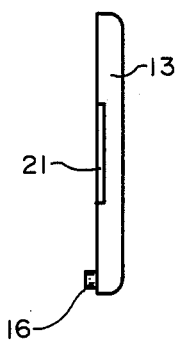
FIG. 5 is an end view of the member shown in FIG. 3.
Figure 6:
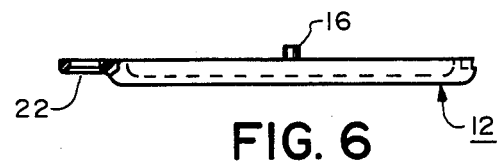
FIG. 6 is a side view of the member shown in FIG. 3.

In FIG. 2 a continuous key ring 26 containing a key 27 is shown attached to case 10 in the same way key chain 24 is attached to case 10. When members 11 and 12 are mated as shown in FIG. 2 pin 16 is inserted in hole 17 and pin 20 is inserted in hole 19 and shoulder 13 and 18 engage to form an enclosed space for condom package 15.

The case is illustrated herein with both members being formed of transparent plastic material. However, one or both members may be formed of or coated with an opaque material such that the contents of the case would not be seen until the case is opened. Further, the case may be enlarged to hold more than the single condom shown in FIG. 1. Of course, unpackaged condoms may be used instead of the packaged condom illustrated. The case may be square, circular or any other shape instead of rectangular so long as the case is capable of containing at least one condom. Also, whether the case is made partly or wholly transparent or opaque, any desired advertising matter or other type of printed/pictoral information may be printed directly on the surfaces of the case.

Various other changes may be made in the specific illustrative embodiments of the invention shown and/or described herein without departing from the scope of the invention as defined in the affended claims.

Having fully described my invention I claim:

1. A key holder and condom case comprising:

Two matable members formed of transparent plastic material, each having a recessed surface to form an enclosure when mated;

at least one condom arranged in said enclosure;

means having openings therein formed on each member;

continuous holder means extending through said openings;

said matable members comprising identically configured members, each having an engageable, peripheral shoulder surrounding a recessed surface to form said enclosure when engaged;

engageable locking pins and associated locking apertures formed on said shoulders for releasably locking said member to each other when said pins and apertures are engaged;

at least one key also arranged on said continuous holder means; and means formed on said shoulders to facilitate separating said members to open said case when said members are engaged and locked together.

* * * * *